(12) United States Patent
Meng et al.

(10) Patent No.: US 11,597,920 B2
(45) Date of Patent: Mar. 7, 2023

(54) COMPOSITIONS AND METHODS FOR ENHANCING REVERSE TRANSCRIPTASE ACTIVITY AND/OR REDUCING THE INHIBITION OF REVERSE TRANSCRIPTASE

(71) Applicant: BIO-RAD LABORATORIES, INC., Hercules, CA (US)

(72) Inventors: Xiangdong Meng, Albany, CA (US); Xiaosong Gong, Richmond, CA (US); Cindy C T Wan, San Francisco, CA (US)

(73) Assignee: BIO-RAD LABORATORIES, INC., Hercules, CA (US)

( * ) Notice: Subject to any disclaimer, the term of this patent is extended or adjusted under 35 U.S.C. 154(b) by 82 days.

(21) Appl. No.: 16/911,421

(22) Filed: Jun. 25, 2020

(65) Prior Publication Data
US 2020/0407706 A1    Dec. 31, 2020

Related U.S. Application Data

(60) Provisional application No. 62/866,182, filed on Jun. 25, 2019.

(51) Int. Cl.
| | |
|---|---|
| *C12N 9/12* | (2006.01) |
| *C12N 9/96* | (2006.01) |
| *C12N 15/11* | (2006.01) |

(52) U.S. Cl.
CPC .............. *C12N 9/96* (2013.01); *C12N 9/1276* (2013.01); *C12N 15/11* (2013.01); *C12Y 207/07049* (2013.01); *C12N 2310/315* (2013.01)

(58) Field of Classification Search
None
See application file for complete search history.

(56) References Cited

U.S. PATENT DOCUMENTS

| | | |
|---|---|---|
| 7,264,932 B2 | 9/2007 | Latham et al. |
| 7,638,307 B2 | 12/2009 | Hantash |
| 8,338,094 B2 | 12/2012 | Gong et al. |
| 8,859,205 B2 | 10/2014 | Gong et al. |
| 8,962,001 B2 | 2/2015 | Raines et al. |
| 9,005,895 B2 | 4/2015 | Woo et al. |
| 9,200,318 B2 | 12/2015 | Gong et al. |
| 9,758,812 B2 | 9/2017 | Fang et al. |
| 9,896,682 B2 | 2/2018 | Gong et al. |
| 10,053,676 B2 | 8/2018 | Cheng |
| 2005/0266417 A1 | 12/2005 | Barany et al. |
| 2009/0042197 A1 | 2/2009 | Hayashizaki et al. |
| 2017/0275685 A1* | 9/2017 | Hayashi ............... C12Q 1/6853 |
| 2017/0356026 A1 | 12/2017 | Fang et al. |
| 2018/0002739 A1 | 1/2018 | Wangh et al. |
| 2019/0032124 A1 | 1/2019 | Vijayan et al. |

FOREIGN PATENT DOCUMENTS

| | | |
|---|---|---|
| CN | 102177237 B | 10/2013 |
| WO | WO 2017/136782 | 8/2017 |
| WO | WO 2018/045181 | 3/2018 |

OTHER PUBLICATIONS

Earl et al., Polyvinylsulfonic acid: A Low-cost RNase inhibitor for enhanced RNA preservation and cell-free translation, Bioengineered, vol. 9, No. 1, pp. 90-97, 2018.*
Affymetrix Two-step RT-PCT kit user instructions; product No. 78355A; Mar. 2002.
Earl, C et al., 2018, "Polyvinylsulfonic acid: A Low-cost RNase inhibitor for enhanced RNA preservation and cell-free protein translation." Bioengineered, 2018, vol. 9, No. 1, pp. 90-97. https://doi.org/10.1080/21655979. 2017.1313648 (Published online: Jun. 29, 2017).
Smith et al., "Potent Inhibition of Ribonuclease A by Oligo(vinylsulfonic Acid)." JBC, Jun. 6, 2003, vol. 278 No. 23, pp. 20934-20938.
Yu, S.-C et al. "Yeast transformation efficiency is enhanced by TORC1- and eisosome-dependent signaling" *MicrobiologyOpen*, 2019, pp. 1-10, vol. 8, No. 5, e730.
International Search Report and Written Opinion in International Application No. PCT/US2020/039479, dated Oct. 14, 2020, pp. 1-13.

* cited by examiner

*Primary Examiner* — Richard G Hutson
(74) *Attorney, Agent, or Firm* — Saliwanchik, Lloyd & Eisenschenk

(57) ABSTRACT

The subject application pertains to compositions and methods for enhancing reverse transcriptase (RT) activity and/or reducing the inhibition of RT by inhibitors, such as formalin, tannic acid and/or heparin. In some embodiments, RT inhibition is reduced by the addition of potassium glutamate, histidine hydrochloride monohydrate, poloxamer 188, or any combination thereof to a reaction mixture comprising a polymerase. In other embodiments, RT is enhanced through the addition of a polyvinyl sulfonic acid sodium salt (PVSA) to a reaction mixture. The subject application also provides oligonucleotide primers for use in the reverse transcription of target sequences and its enhancement. These primers have high GC content or low GC content. Methods of using a RT inhibition reducer or a RT enhancer in a composition with an RNA template and RT improves RT yield, RT sensitivity, or RT tolerance to various chemicals are also provided.

22 Claims, 3 Drawing Sheets
Specification includes a Sequence Listing.

SEQUENCE LISTING

```
<160> NUMBER OF SEQ ID NOS: 23

<210> SEQ ID NO 1
<211> LENGTH: 19
<212> TYPE: DNA
<213> ORGANISM: Artificial Sequence
<220> FEATURE:
<223> OTHER INFORMATION: primer

<400> SEQUENCE: 1
gaaggtgaag gtcggagtc                                              19

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
gaagatggtg atgggatttc                                             20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
```
aggaattccc agtaagtgcg                                              20

<210> SEQ ID NO 4
<211> LENGTH: 19
<212> TYPE: DNA
<213> ORGANISM: Artificial Sequence
<220> FEATURE:
<223> OTHER INFORMATION: primer

<400> SEQUENCE: 4
gcctcactaa accatccaa                                               19

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
agctctctaa tcaccatgac                                              20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
aatagaagct ggcaacacaa                                              20

<210> SEQ ID NO 7
<211> LENGTH: 24
<212> TYPE: DNA
<213> ORGANISM: Artificial Sequence
<220> FEATURE:
<223> OTHER INFORMATION: primer

<400> SEQUENCE: 7
tgatgcagaa gagattcatt ctaa                                         24

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
tcatttctag ttggagacac t                                            21

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
attcagacat gagacggttt                                              20

<210> SEQ ID NO 10
<211> LENGTH: 20
<212> TYPE: DNA

```
<213> ORGANISM: Artificial Sequence
<220> FEATURE:
<223> OTHER INFORMATION: primer

<400> SEQUENCE: 10
aaagcttgaa gccaccatta                                                   20

<210> SEQ ID NO 11
<211> LENGTH: 24
<212> TYPE: DNA
<213> ORGANISM: Artificial Sequence
<220> FEATURE:
<223> OTHER INFORMATION: primer

<400> SEQUENCE: 11
gccatatttc atatcttcaa cact                                              24

<210> SEQ ID NO 12
<211> LENGTH: 22
<212> TYPE: DNA
<213> ORGANISM: Artificial Sequence
<220> FEATURE:
<223> OTHER INFORMATION: primer

<400> SEQUENCE: 12
agaaacctct aggaattagt ga                                                22

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
gaagttgatg tcgcagccct                                                   20

<210> SEQ ID NO 14
<211> LENGTH: 18
<212> TYPE: DNA
<213> ORGANISM: Artificial Sequence
<220> FEATURE:
<223> OTHER INFORMATION: primer

<400> SEQUENCE: 14
acttctcttt cccggcgc                                                     18

<210> SEQ ID NO 15
<211> LENGTH: 21
<212> TYPE: DNA
<213> ORGANISM: Artificial Sequence
<220> FEATURE:
<223> OTHER INFORMATION: primer

<400> SEQUENCE: 15
gttgctgtgg ctgagatttg g                                                 21

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
cattttcacc tgctcgcgaa                                                   20
```

```
<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17
gttgctgtgg ctgagatttg g                                              21

<210> SEQ ID NO 18
<211> LENGTH: 15
<212> TYPE: DNA
<213> ORGANISM: Artificial Sequence
<220> FEATURE:
<223> OTHER INFORMATION: primer

<400> SEQUENCE: 18
aacagccccg ggcac                                                     15

<210> SEQ ID NO 19
<211> LENGTH: 21
<212> TYPE: DNA
<213> ORGANISM: Artificial Sequence
<220> FEATURE:
<223> OTHER INFORMATION: primer

<400> SEQUENCE: 19
gttgctgtgg ctgagatttg g                                              21

<210> SEQ ID NO 20
<211> LENGTH: 16
<212> TYPE: DNA
<213> ORGANISM: Artificial Sequence
<220> FEATURE:
<223> OTHER INFORMATION: primer

<400> SEQUENCE: 20
agggagagga gcgagc                                                    16

<210> SEQ ID NO 21
<211> LENGTH: 10
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(10)
<223> OTHER INFORMATION: n is a, c, g, or t

<400> SEQUENCE: 21 nnnnnnnnnn                                                           10

<210> SEQ ID NO 22
<211> LENGTH: 11
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(11)
<223> OTHER INFORMATION: n is a, c, g, or t

<400> SEQUENCE: 22
```

| nnnnnnnnn n | 11 |

```
<210> SEQ ID NO 23
<211> LENGTH: 12
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(12)
<223> OTHER INFORMATION: n is a, c, g, or t

<400> SEQUENCE: 23
```

| nnnnnnnnnn nn | 12 |

COMPOSITIONS AND METHODS FOR ENHANCING REVERSE TRANSCRIPTASE ACTIVITY AND/OR REDUCING THE INHIBITION OF REVERSE TRANSCRIPTASE

CROSS-REFERENCE TO RELATED APPLICATION

This application claims the benefit of U.S. Provisional Application 62/866,182, filed on Jun. 25, 2019, which is hereby incorporated by reference in its entirety.

The Sequence Listing for this application is labeled "Seq-List.txt" which was created on Jun. 20, 2020 and is 5 KB. The entire content of the sequence listing is incorporated herein by reference in its entirety.

BRIEF SUMMARY OF THE INVENTION

The inventors have surprisingly discovered that reverse transcriptase (RT) activity can be enhanced by performing the synthesis of complementary DNA (cDNA) from an RNA template having high and low GC content in the presence of oligonucleotide primers that contain randomized primers having high and/or low GC content. It has also been surprisingly discovered that reverse transcriptase inhibition by heparin, formalin, or tannic acid can be reduced by performing the synthesis of cDNA by RT in the presence of additives, such as potassium glutamate, histidine hydrochloride monohydrate and/or poloxamer 188. It has also been surprisingly found that reverse transcriptase (RT) activity can be enhanced by performing the synthesis of complementary DNA (cDNA) from an RNA template in the presence of salts of polyvinyl sulfonic acid (PVSA), for example, the sodium salt of PVSA. Various reaction mixtures comprising additives disclosed herein are also provided.

DETAILED DISCLOSURE OF THE INVENTION

Figure 1:
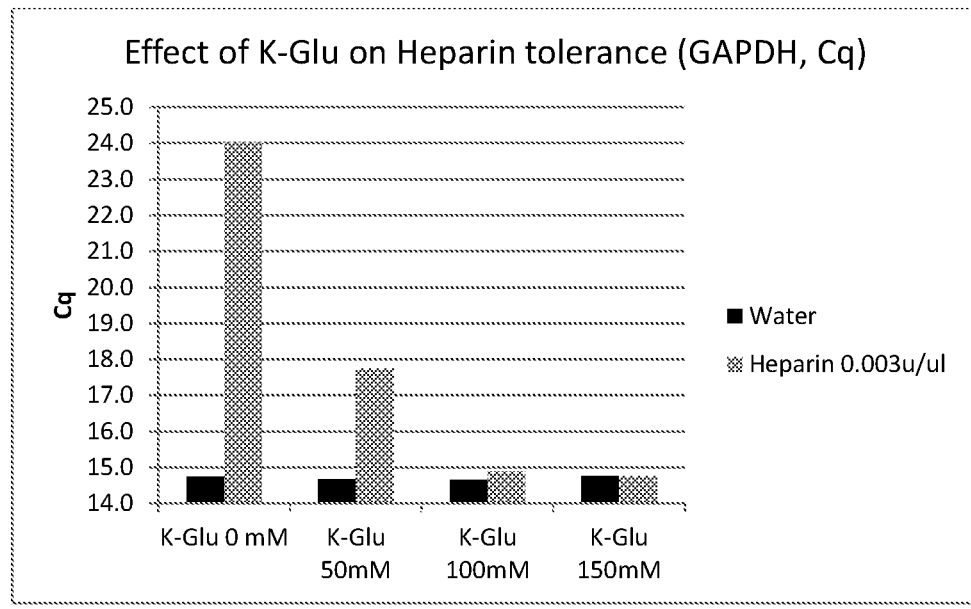
FIG. 1. Effect of K-Glu (Potassium Glutamate) on Heparin tolerance. Potassium Glutamate improves RT tolerance to Heparin. Heparin (0.003 U/µl) in the RT reaction causes Cq delay over 7, while with 100 mM K-Glu present, the Cq delay is less than 1.
Figure 1:
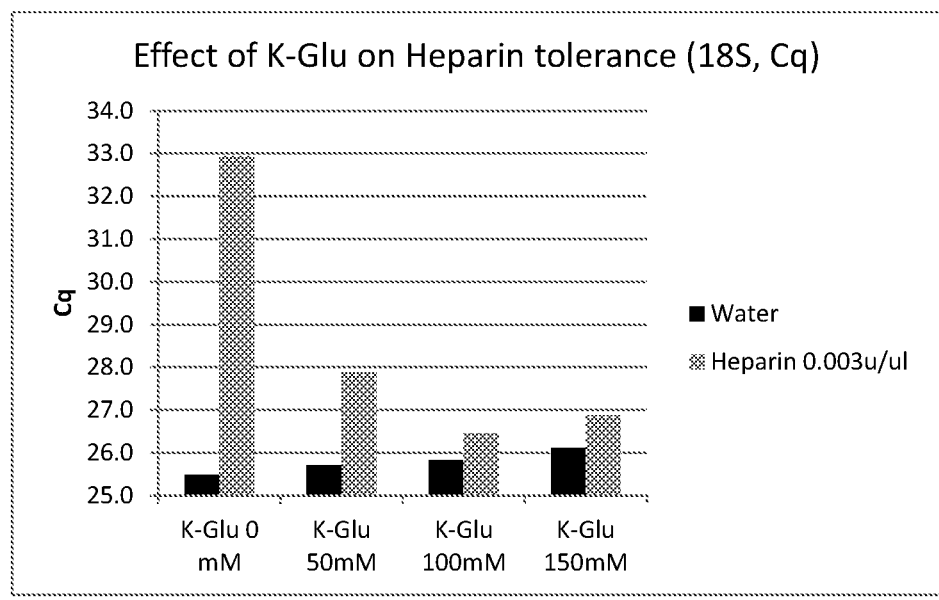
Figure 2:
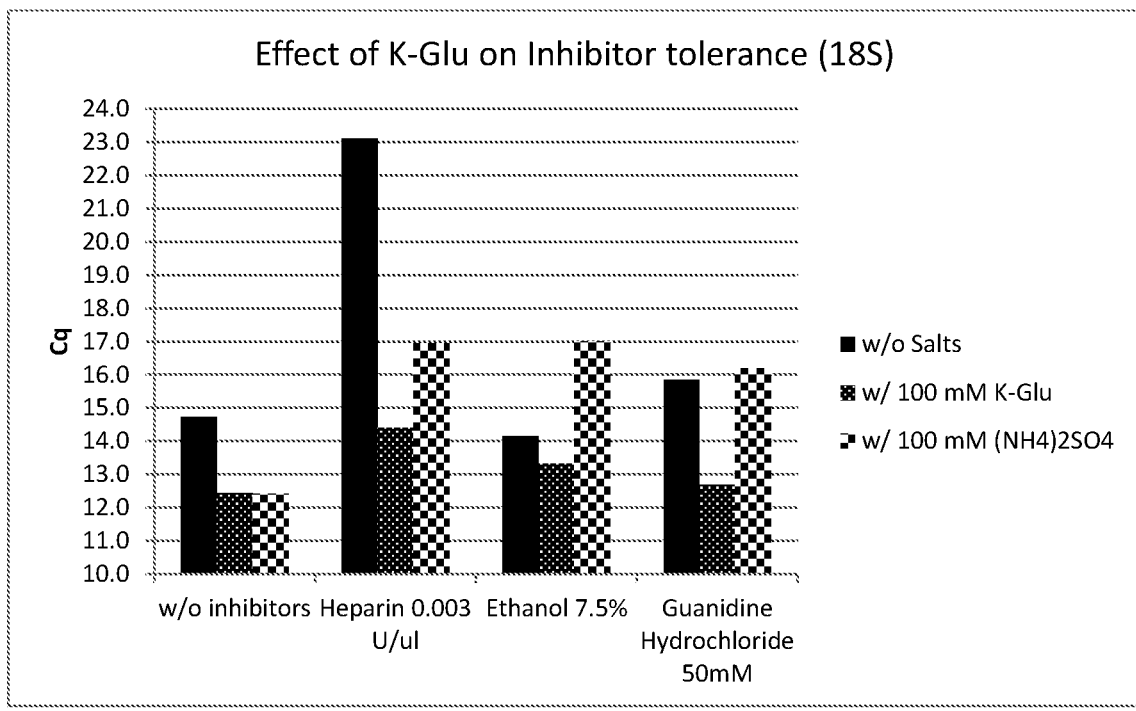
FIG. 2. K-Glu (Potassium Glutamate) improves Heparin tolerance without compromising tolerance to other inhibitors. Potassium Glutamate improves Heparin tolerance without compromising tolerance to 7.5% Ethanol and 50 mM Guanidinum hydrochloride. (NH4)2SO4 also improves Heparin tolerance though not as effect as K-Glu, but it compromises Ethanol and GC tolerance.

As used herein, the singular forms "a", "an" and "the" are intended to include the plural forms as well, unless the context clearly indicates otherwise. Furthermore, to the extent that the terms "containing", "including", "includes", "having", "has", "with", or grammatical variants thereof are used in either the detailed description and/or the claims, such terms are intended to be inclusive in a manner similar to the term "comprising". The transitional terms/phrases (and any grammatical variations thereof) "comprising", "comprises", "comprise", "consisting essentially of", "consists essentially of", "consisting" and "consists" can be used interchangeably.

The phrases "consisting essentially of" or "consists essentially of" indicate that the claim encompasses embodiments containing the specified materials or steps and those that do not materially affect the basic and novel characteristic(s) of the claim.

The term "about" or "approximately" means within an acceptable error range for the particular value as determined by one of ordinary skill in the art, which will depend in part on how the value is measured or determined, i.e., the limitations of the measurement system. The terms "about" and "approximately" are meant to encompass a range of ±20%, ±10% or ±5% of a given value. Thus, in the context of compositions containing amounts of ingredients where the terms "about" or "approximately" are used, these compositions can contain the stated amount of the ingredient with a variation (error range) of 0-10% around the value (X±10%).

In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. Values having at least two significant digits within a range are envisioned, for example, a range of 5-10 indicates all the values between 5.0 and 10.0 as well as between 5.00 and 10.00 including the terminal values.

The terms "simultaneous" or "simultaneously" as applied to the method of synthesizing cDNA from an RNA template using RT refers to adding one or more components to the composition at the same time, or at two different time points that are separated by no more than 3 minutes. The phrase "after or before" as applied to methods of synthesizing cDNA from template RNA refers to adding more than one composition at two different time points that are separated by more than 3 minutes, e.g., about 5 minutes, 30 minutes, 1 hour, about 2 hours, about 5 hours, or even longer.

Various techniques for performing quantitative amplification of a nucleic acid are known. These techniques include use of 5' to 3' exonuclease assays, e.g., Taqman™ probes (see, e.g., U.S. Pat. Nos. 5,210,015 and 5,487,972, Heid et al., Genome Res. 6:986-994, 1996; Holland et al., Proc. Nat'l Acad. Sci. USA 88:7276-7280, 1991; and Lee et al., Nuc. Acids Res. 21:3761-3766, 1993). Other methodologies employ one or more probe oligonucleotides that are structured such that a change in fluorescence is generated when the oligonucleotide(s) is hybridized to a target nucleic acid.

For example, one such method involves a dual fluorophore approach that exploits fluorescence resonance energy transfer (FRET), e.g., LightCycler™ hybridization probes, where two oligo probes anneal to the amplicon (e.g., U.S. Pat. No. 6,174,670). Other examples of labeled oligonucleotides that are structured to emit a signal when bound to a nucleic acid or incorporated into an extension product include: Scorpions™ probes (e.g., Whitcombe et al., Nature Biotechnology 17:804-807, 1999, and U.S. Pat. No. 6,326,145), Sunrise (or Ampliflour™) primers (e.g., Nazarenko et al., Nuc. Acids Res. 25:2516-2521, 1997, and U.S. Pat. No. 6,117,635), LUX™ primers and Molecular Beacons™ probes (e.g., Tyagi et al., Nature Biotechnology 14:303-308, 1996 and U.S. Pat. No. 5,989,823).

The present invention provides a method for amplifying a nucleic acid molecule. The method involves mixing an RNA template with a composition comprising a reverse transcriptase, an additive as described herein that reduces RT inhibition and/or increases RT efficiency and/or a polymerase.

In RT-PCR, the reaction mixture is first incubated (in an appropriate buffering agent) at a temperature sufficient to allow synthesis of a DNA molecule complementary to at least a portion of an RNA template. Components of a reverse transcription reaction mixture typically include an RNA template and a DNA primer from which the complementary DNA (cDNA) is produced; a nucleic acid polymerase that exhibits reverse transcriptase activity; and the appropriate nucleotide building blocks (dNTPs) needed for nucleic acid synthesis. For the purposes of this invention, cDNA is defined as any DNA molecule whose nucleic acid sequence is complementary to an RNA molecule.

An RNA template is defined as any RNA molecule used to provide a nucleic acid sequence from which a cDNA molecule can be synthesized. The synthesis of cDNA from an RNA template is typically accomplished by utilizing a nucleic acid polymerase that exhibits reverse transcriptase activity. For the purposes of this invention, reverse transcriptase activity refers to the ability of an enzyme to polymerize a cDNA molecule from an RNA template, and the term "reverse transcriptase" (RT) broadly refers to any enzyme possessing reverse transcriptase activity. Reverse transcription typically occurs in a temperature range from about 20° C. to about 75° C., preferably from about 35° C. to about 70° C.

After reverse transcription of an RNA template to produce a cDNA molecule, the cDNA is incubated (in an appropriate buffering agent) under conditions sufficient for replication of the cDNA molecule. The reaction mixture can be the same as that of the previous reverse transcription reaction mixture, as employed in coupled (also called continuous, or one-step) RT-PCR, or the reaction mixture can comprise an aliquot of the previous reverse transcription reaction mixture and can be further modified for nucleic acid replication, as in uncoupled (or two-step) RT-PCR. Components of a replication reaction mixture typically include a nucleic acid template (in this instance the cDNA); DNA primers; a nucleic acid polymerase; and the appropriate nucleotide building blocks needed for nucleic acid synthesis. Nucleic acid replication refers to the polymerization of a nucleic acid whose sequence is determined by, and complementary to, another nucleic acid. DNA replication, as used herein, is synonymous with DNA amplification. Preferably DNA amplification occurs repetitively, thus replicating both strands of the nucleic acid sequence, i.e., DNA complementary to the RNA template, and DNA whose nucleic acid sequence is substantially identical to the RNA template. Repetitive, or cyclic, DNA replication can be advantageously accomplished using a thermostable polymerase in a Polymerase Chain Reaction (PCR).

PCR is a technique well known in the art. PCR is used to amplify nucleic acids by subjecting a reaction mixture to cycles of: (i) nucleic acid denaturation, (ii) oligonucleotide primer annealing, and (iii) nucleic acid polymerization. Preferred reaction conditions for amplification comprise thermocycling, i.e., alternating the temperature of the reaction mixture to facilitate each of the steps of the PCR cycle. PCR is typically extended through multiple cycles of denaturation, annealing and replication, augmented (optionally and preferably) with an initial prolonged denaturation step and a final prolonged extension (polymerization) step. Thermocycling typically occurs within a temperature range of between about 23° C. to about 100° C., and preferably between about 37° C. to about 95° C. Nucleic acid denaturation typically occurs between about 90° C. to about 100° C., preferably about 94° C. Annealing typically occurs between about 37° C. to about 75° C., preferably about 60° C. Polymerization typically occurs between about 55° C. to about 80° C., preferably about 72° C. The number of thermocycles varies immensely, depending upon practitioner preference, the quantity of DNA template used, and the quantity of DNA product desired. Preferably, the number of PCR cycles ranges from about 5 to about 99, more preferably greater than about 20 cycles, most preferably about 40 cycles.

Primers should be designed according to standard PCR guidelines with a length of 18 to 25 nucleotides, and a GC content of 40% to 65%. Primer design should avoid internal secondary structure, and complementarity at the 3' ends within each primer and primer pair. Optimal results can require titration of primer concentration between 100 and 500 nM. A final concentration of 300 nM per primer is effective for most reactions. In general, reaction efficiency and/or specificity can be optimized using equal concentrations of each primer. For best results, amplicon size should be limited to 50-200 bp for quantitative RT-PCR.

Suggested input quantities of template are: 0.1 pg to 100 ng total RNA; 10 fg to 100 ng polyA(+) RNA. First strand synthesis can be performed between 40° C. and 52° C. Optimal results are generally obtained with a 10-minute incubation at 50° C.

A. RNA Template

The template RNA can be any ribonucleic acid of interest, known or unknown to the practitioner. Template RNA can be artificially synthesized or isolated from natural sources. In some embodiments, the RNA template can be a ribonucleic acid such as RNA, mRNA, piRNA, tRNA, rRNA, ncRNA, gRNA, shRNA, siRNA, snRNA, miRNA and snoRNA. Preferably the RNA is mRNA. More preferably the RNA is biologically active or encodes a biologically active polypeptide. The RNA template can also be present in any useful amount. In some embodiments, the RNA template concentration is 50 pg/µL or less. One of skill in the art will appreciate that other RNA template concentrations are useful in the present invention.

B. Reverse Transcriptase

Reverse transcriptases useful in the present invention can be any polymerase that exhibits reverse transcriptase activity. Preferred enzymes include those that exhibit reduced RNase H activity. Several reverse transcriptases are known in the art and are commercially available (e.g., from Boehringer Mannheim Corp., Indianapolis, Ind.; Life Technologies, Inc., Rockville, Md.; New England Biolabs, Inc., Beverley, Mass.; Perkin Elmer Corp., Norwalk, Conn.;

Pharmacia LKB Biotechnology, Inc., Piscataway, N.J.; Qiagen, Inc., Valencia, Calif.; Stratagene, La Jolla, Calif.). In some embodiments, the reverse transcriptase can be Avian Myeloblastosis Virus reverse transcriptase (AMV-RT), Moloney Murine Leukemia Virus reverse transcriptase (M-MLV-RT), Human Immunovirus reverse transcriptase (HIV-RT), EIAV-RT, RAV2-RT, C. hydrogenoformans DNA Polymerase, rTth DNA polymerase, SUPERSCRIPT I, SUPERSCRIPT II, and mutants, variants and derivatives thereof. It is to be understood that a variety of reverse transcriptases can be used in the present invention, including reverse transcriptases not specifically disclosed above, without departing from the scope or preferred embodiments disclosed herein.

C. DNA Polymerase

DNA polymerases useful in the present invention can be any polymerase capable of replicating a DNA molecule. Preferred DNA polymerases are thermostable polymerases, which are especially useful in PCR. Thermostable polymerases are isolated from a wide variety of thermophilic bacteria, such as *Thermus aquaticus* (Taq), *Thermus brockianus* (Tbr), *Thermus flavus* (Tfl), *Thermus ruber* (Tru), *Thermus thermophilus* (Tth), *Thermococcus litoralis* (Tli) and other species of the *Thermococcus* genus, *Thermoplasma acidophilum* (Tac), *Thermotoga neapolitana* (Tne), *Thermotoga maritima* (Tma), and other species of the *Thermotoga* genus, *Pyrococcus furiosus* (Pfu), *Pyrococcus woesei* (Pwo) and other species of the *Pyrococcus* genus, *Bacillus sterothemophilus* (Bst), *Sulfolobus acidocaldarius* (Sac) *Sulfolobus solfataricus* (Sso), *Pyrodictium occultum* (Poc), *Pyrodictium abyssi* (Pab), and *Methanobacterium thermoautotrophicum* (Mth), and mutants, variants or derivatives thereof.

Many DNA polymerases are known in the art and are commercially available (e.g., from Boehringer Mannheim Corp., Indianapolis, Ind.; Life Technologies, Inc., Rockville, Md.; New England Biolabs, Inc., Beverley, Mass.; Perkin Elmer Corp., Norwalk, Conn.; Pharmacia LKB Biotechnology, Inc., Piscataway, N.J.; Qiagen, Inc., Valencia, Calif.; Stratagene, La Jolla, Calif.). In some embodiments, the DNA polymerase can be Taq, Tbr, Tfl, Tru, Tth, Tli, Tac, Tne, Tma, Tih, Tfi, Pfu, Pwo, Kod, Bst, Sac, Sso, Poc, Pab, Mth, Pho, ES4, VENT™, DEEPVENT™, and active mutants, variants and derivatives thereof. It is to be understood that a variety of DNA polymerases can be used in the present invention, including DNA polymerases not specifically disclosed above, without departing from the scope or preferred embodiments thereof.

The reverse transcriptase can be present in any appropriate ratio to the DNA polymerase. In some embodiments, the ratio of reverse transcriptase to DNA polymerase in unit activity is greater than or equal to 3. One of skill in the art will appreciate that other reverse transcriptase to DNA polymerase ratios are useful in the present invention.

D. Additives for Improving Efficiency of Reverse Transcription

In certain aspects, additives are provided to improve efficiency of reverse transcription, improve inhibitor tolerance and/or prevent RNA degradation. Thus, the additives find use in reverse transcription and PCR amplification reactions, such as qPCR. Reaction mixtures comprising the additives can include other components, such as polymerases and/or reverse transcriptases. The inclusion of the additive in a reaction mixture is sufficient to produce RT-qPCR results with efficiency close to 100%, and that is at least 10, or 40, or 50% or 100% more as compared to a control mixture lacking the additive. These additives, such as poloxamer 188, histidine, such as histidine hydrochloride monohydrate, glutamate and/or salts thereof, reduce the inhibition of amplification reactions caused by heparin, formalin and/or tannic acid. In some aspects of the invention, the additive, for example, PVSA or a salt thereof, can improve the efficiency of amplification reactions in the presence or absence of heparin, formalin and/or tannic acid.

Figure 3:
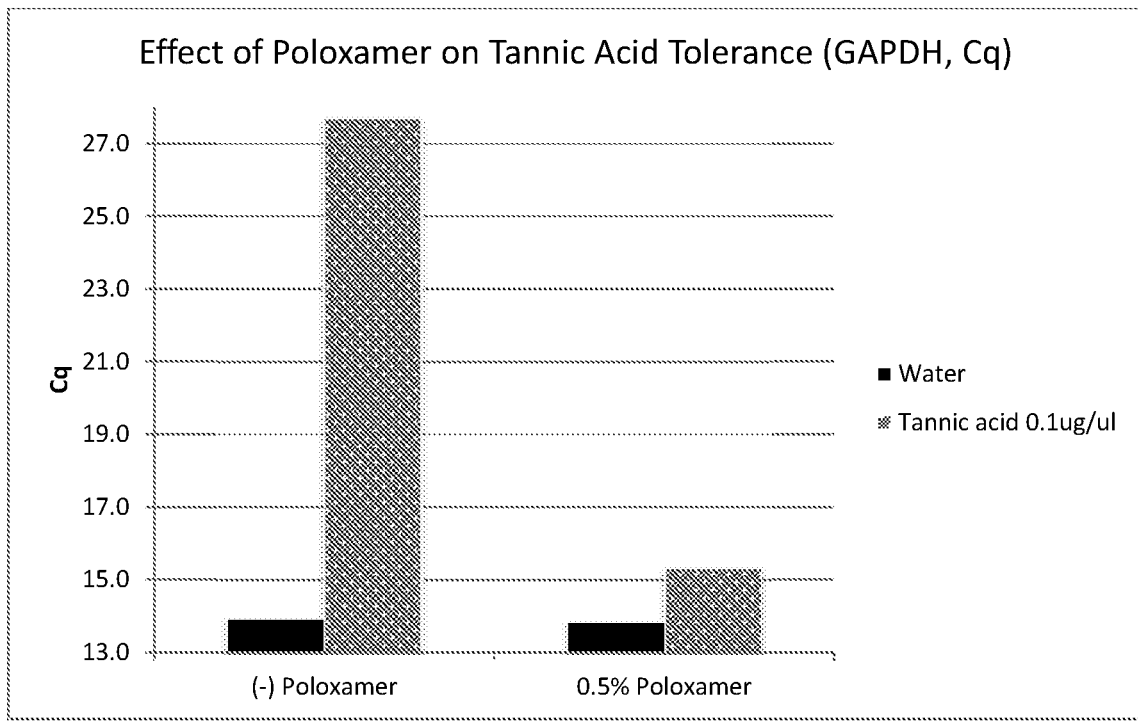
FIG. 3. Effect of Poloxamer on tannic acid tolerance. Poloxamer improves tannic acid tolerance. Tannic acid at 0.1 µg/µl in the RT reaction severely inhibits the RT process and causes Cq delay over 13, while the presence of 0.5% Poloxamer effectively improves RT tolerance to tannic acid (less than 2 Cq delay).

In some embodiments, the additive is histidine or histidine hydrochloride monohydrate and can be included in an amplification reaction to improve RT efficiency, particularly in the presence of formalin and/or heparin. In methods of the present invention, millimolar concentrations of histidine and/or histidine hydrochloride monohydrate have been found to be effective for improving the reaction efficiency of amplification reactions. Concentrations of about 0.01 mM to about 100 mM histidine or histidine hydrochloride monohydrate are used in methods and kits of the present invention. In still further embodiments, histidine or histidine hydrochloride monohydrate concentrations of about 1 mM to about 50 mM, about 5 mM to about 40 mM, about 2.5 mM to about 30 mM, about 5 mM to about 30 mM, about 10 mM to about 30 mM, about 10 mM to about 25 mM, or about 15 mM to about 20 mM are used in methods and kits of the invention. As shown in FIG. 3, addition of histidine to reaction mixtures containing formalin improved the efficiency of the amplification reaction as compared to a control lacking histidine.

Figure 4:
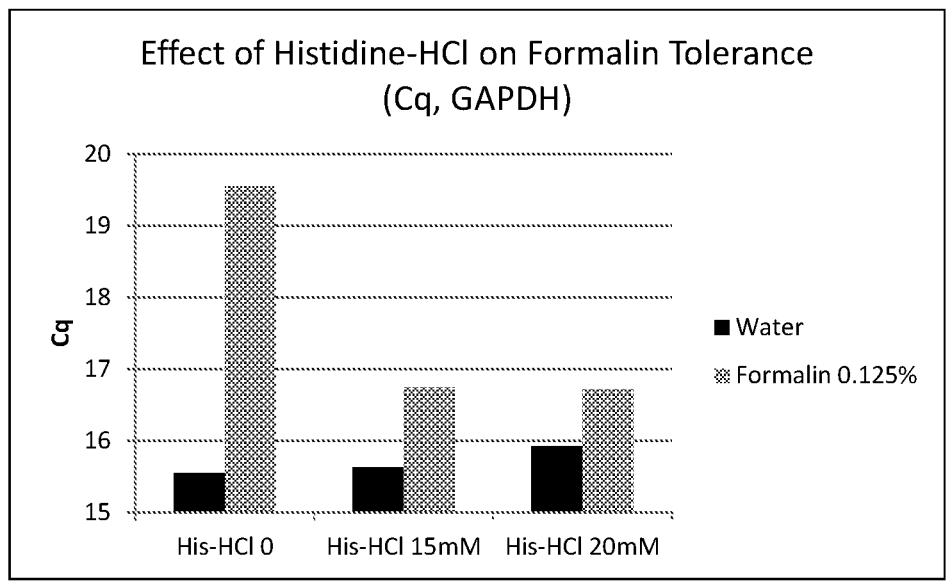
FIG. 4. Effect of Histidine-HCl on Formalin tolerance. His-HCl improves formalin tolerance during RT reaction. Without His-HCl, RT products have about 4 Cq delay, while with 15 to 20 mM His-Cl present, there is less than 1 Cq delay.
Figure 5:
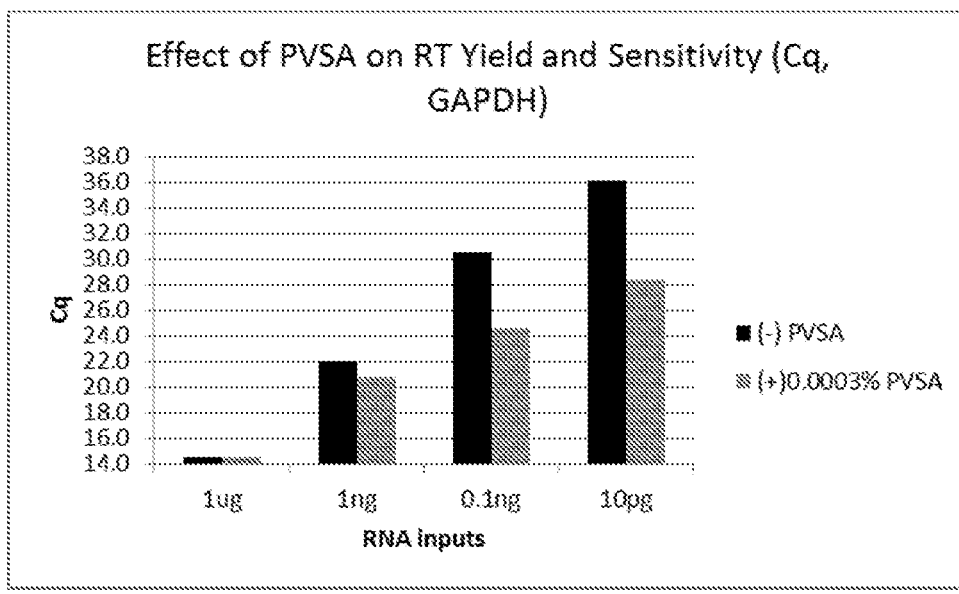
FIG. 5. Effect of PVSA on RT yield and Sensitivity. When RNA inputs in the RT reaction are limited (decreased), PVSA can improve RT yield and make the RNA detection more sensitive. For example, here it shows that at 0.1 ng RNA input, PVSA can improve Cq by about 3 cycles (earlier than w/o PVSA), and increase sensitivity about 10 folds.

In some embodiments, the additive is a poloxamer, such as poloxamer 188, that is included in an amplification reaction mixture to improve efficiency, particularly in the presence of tannic acid. In methods of the present invention, poloxamer is added in amounts ranging from about 0.01% to about 5% (v/v) of the reaction mixture. In various embodiments, poloxamer is added in an amount (v/v) that is about 0.05% to about 4%, about 0.1% to about 3%, about 0.25% to about 2%, about 0.3% to about 1%, about 0.3% to about 0.75% or about 0.3% to about 0.6% or about 0.5%. As shown in FIG. 4, addition of poloxamer to reaction mixtures containing tannic acid improved the efficiency of the amplification reaction as compared to a control lacking poloxamer. Concentrations/amounts of poloxamer present in a reaction mixture are provided as v/v % poloxamer content.

In still further embodiments, glutamate or salts thereof (for example, ammonium, calcium, magnesium, monosodium, and/or potassium salts) can be included in an amplification reaction to improve efficiency, particularly in the presence of heparin. For example, potassium glutamate is present in an amplification reaction mixture at concentrations of about 5 mM to about 250 mM, about 10 mM to about 400 mM, about 10 mM to about 300 mM, about 10 mM to about 250 mM, about 10 mM to about 200 mM, about 10 mM to about 150 mM, about 15 mM to about 400 mM, about 15 mM to about 300 mM, about 15 mM to about 250 mM, about 15 mM to about 200 mM or about 15 mM to about 150 mM.

In yet other embodiments, PVSA is included in an amplification reaction to improve RT efficiency and/or sensitivity. PVSA can be provided at a concentration (v/v) of about 0.0001% to about 0.002%, about 0.0001% to about 0.005%, about 0.0001% to about 0.004%, about 0.0001% to about 0.003%, about 0.0001% to about 0.002%, or about 0.0001% to about 0.001%. Concentrations/amounts of PVSA present in a reaction mixture are provided as v/v % PVSA content.

Another additive that can be provided to a reaction mixture for the purposes of enhancing RT are one or more oligonucleotide primers as described herein. The disclosed one or more oligonucleotides can be used in combination with the other disclosed additives or alone. These oligonucleotide primers are five (5) to twelve (12) nucleotides in length and are composed of random nucleotides selected from adenine (A), cytosine (C), guanine (G), and thymine (T). Thus, the oligonucleotide primers comprise the sequences of $X_1$-$X_2$-$X_3$-$X_4$-$X_5$, $X_1$-$X_2$-$X_3$-$X_4$-$X_5$-$X_6$, $X_1$-$X_2$-$X_3$-$X_4$-$X_5$-$X_6$-$X_7$, $X_1$-$X_2$-$X_3$-$X_4$-$X_5$-$X_6$-$X_7$-$X_8$, $X_1$-$X_2$-$X_3$-$X_4$-$X_5$-$X_6$-$X_7$-$X_8$-$X_9$, $X_1$-$X_2$-$X_3$-$X_4$-$X_5$-$X_6$-$X_7$-$X_8$-$X_9$-$X_{10}$ (SEQ ID NO: 21), $X_1$-$X_2$-$X_3$-$X_4$-$X_5$-$X_6$-$X_7$-$X_8$-$X_9$-$X_{10}$-$X_{11}$ (SEQ ID NO: 22), or $X_1$-$X_2$-$X_3$-$X_4$-$X_5$-$X_6$-$X_7$-$X_8$-$X_9$-$X_{10}$-$X_{11}$-$X_{12}$ (SEQ ID NO: 23). If desired, the primers can contain one or more phosphorothioate bonds at any position within the oligonucleotide. For example, one or more phosphorothioate bonds can be introduced between the ultimate, penultimate and/or antepenultimate nucleotides at the 5' or 3' ends of the oligonucleotides. Alternatively, one or more phosphorothioate bonds can be introduced between the ultimate, penultimate and/or antepenultimate nucleotides at both the 5' and 3' ends of the oligonucleotides. In some embodiments, the oligonucleotide primers are random. Other embodiments provide oligonucleotide primers that have high GC or high AT content. For the purposes of this application, at least 60% of the nucleotides in a high CG content primer are G and/or C. Likewise, at least 60% of the nucleotides in a high AT content primer are A and/or T.

Certain embodiments provide an:

a) $X_1$-$X_2$-$X_3$-$X_4$-$X_5$ oligonucleotide sequence that is: a) randomly ordered A and T nucleotides; b) randomly ordered G and C nucleotides; c) at least one but less than five of the nucleotides are randomly selected from a group consisting of: A, G, T, and C, while the remaining nucleotides are randomly selected G and C nucleotides; or d) at least one but less than five of the nucleotides are randomly selected from a group consisting of: A, G, T, and C, while the remaining nucleotides are randomly selected A and T nucleotides;

b) $X_1$-$X_2$-$X_3$-$X_4$-$X_5$-$X_6$ oligonucleotide sequence that is: a) randomly ordered A and T nucleotides; b) randomly ordered G and C nucleotides; c) at least one but less than six of the nucleotides are randomly selected from a group consisting of: A, G, T, and C, while the remaining nucleotides are randomly selected G and C nucleotides; or d) at least one but less than six of the nucleotides are randomly selected from a group consisting of: A, G, T, and C, while the remaining nucleotides are randomly selected A and T nucleotides;

c) $X_1$-$X_2$-$X_3$-$X_4$-$X_5$-$X_6$-$X_7$ oligonucleotide sequence that is: a) randomly ordered A and T nucleotides; b) randomly ordered G and C nucleotides; c) at least one but less than seven of the nucleotides are randomly selected from a group consisting of: A, G, T, and C, while the remaining nucleotides are randomly selected G and C nucleotides; or d) at least one but less than seven of the nucleotides are randomly selected from a group consisting of: A, G, T, and C, while the remaining nucleotides are randomly selected A and T nucleotides;

d) $X_1$-$X_2$-$X_3$-$X_4$-$X_5$-$X_6$-$X_7$-$X_8$ oligonucleotide sequence that is: a) randomly ordered A and T nucleotides; b) randomly ordered G and C nucleotides; c) at least one but less than eight of the nucleotides are randomly selected from a group consisting of: A, G, T, and C, while the remaining nucleotides are randomly selected G and C nucleotides; or d) at least one but less than eight of the nucleotides are randomly selected from a group consisting of: A, G, T, and C, while the remaining nucleotides are randomly selected A and T nucleotides;

e) $X_1$-$X_2$-$X_3$-$X_4$-$X_5$-$X_6$-$X_7$-$X_8$-$X_9$ oligonucleotide sequence that is: a) randomly ordered A and T nucleotides; b) randomly ordered G and C nucleotides; c) at least one but less than nine of the nucleotides are randomly selected from a group consisting of: A, G, T, and C, while the remaining nucleotides are randomly selected G and C nucleotides; or d) at least one but less than nine of the nucleotides are randomly selected from a group consisting of: A, G, T, and C, while the remaining nucleotides are randomly selected A and T nucleotides;

f) $X_1$-$X_2$-$X_3$-$X_4$-$X_5$-$X_6$-$X_7$-$X_8$-$X_9$-$X_{10}$ (SEQ ID NO: 21) oligonucleotide sequence that is: a) randomly ordered A and T nucleotides; b) randomly ordered G and C nucleotides; c) at least one but less than ten of the nucleotides are randomly selected from a group consisting of: A, G, T, and C, while the remaining nucleotides are randomly selected G and C nucleotides; or d) at least one but less than ten of the nucleotides are randomly selected from a group consisting of: A, G, T, and C, while the remaining nucleotides are randomly selected A and T nucleotides;

g) $X_1$-$X_2$-$X_3$-$X_4$-$X_5$-$X_6$-$X_7$-$X_8$-$X_9$-$X_{10}$-$X_{11}$ (SEQ ID NO: 22) oligonucleotide sequence that is: a) randomly ordered A and T nucleotides; b) randomly ordered G and C nucleotides; c) at least one but less than eleven of the nucleotides are randomly selected from a group consisting of: A, G, T, and C, while the remaining nucleotides are randomly selected G and C nucleotides; or d) at least one but less than eleven of the nucleotides are randomly selected from a group consisting of: A, G, T, and C, while the remaining nucleotides are randomly selected A and T nucleotides;

h) $X_1$-$X_2$-$X_3$-$X_4$-$X_5$-$X_6$-$X_7$-$X_8$-$X_9$-$X_{10}$-$X_{11}$-$X_{12}$ (SEQ ID NO: 23) oligonucleotide sequence that is: a) randomly ordered A and T nucleotides; b) randomly ordered G and C nucleotides; c) at least one but less than twelve of the nucleotides are randomly selected from a group consisting of: A, G, T, and C, while the remaining nucleotides are randomly selected G and C nucleotides; or d) at least one but less than twelve of the nucleotides are randomly selected from a group consisting of: A, G, T, and C, while the remaining nucleotides are randomly selected A and T nucleotides.

In certain embodiments, the oligonucleotide sequence is $dW_n$, where W is A or T and n is an integer selected from 5, 6, 7, 8, 9, 10, 11 or 12. Other embodiments provide an oligonucleotide sequence of $dS_n$, where S is G or C and n is an integer selected from 5, 6, 7, 8, 9, 10, 11 or 12. Yet other embodiments provide an oligonucleotide sequence of $dA_n$, $dG_n$, $dC_n$, or $dT_n$ where n is an integer selected from 5, 6, 7, 8, 9, 10, 11 or 12. Yet other embodiments provide an random oligonucleotide sequence of $X_n$ (referred to as $RX_n$), where n is an integer selected from 5, 6, 7, 8, 9, 10, 11 or 12 and X is any nucleotide as disclosed in subsection H, such as a dNTP, dA, dC, dG or dT. Various combinations of any of the disclosed oligonucleotides can be added to reaction mixtures to enhance RT. Further, the concentrations of primers added to a reaction mixture can be between about 1 μM and about 1000 μM, about 2.5 μM and about 750 μM, 5 μM and about 500 μM, 5 μM and about 250 μM, about 5 μM and about 100 μM, 10 μM and about 500 μM, 10 μM and about 250 μM, 10 μM and about 100 μM or 10 μM and about 50 μM.

With respect to the use of one or more oligonucleotides for enhancing reverse transcriptase activity, the method comprises of the addition of an RNA template to a reaction mixture comprising one or more of the oligonucleotides disclosed herein and incubating the mixture to synthesize complementary DNA to all or a portion of the template RNA. Any combination of oligonucleotides can be used in such a method. For example, the reaction mixture can comprise $RX_n$ and $dW_n$; $RX_n$ and $dS_n$, $RX_n$ and $dW_n$, $RX_n$, dS$_n$ and dW$_n$, RX$_n$ and dT$_n$, RX$_n$, dS$_n$ and dT$_n$, or RX$_n$, dT$_n$, dW$_n$ and dS$_n$, where each n for a given oligonucleotide is independently selected from an integer selected from 5, 6, 7, 8, 9, 10, 11 or 12. In certain embodiments, n is independently selected from 5, 6, 7, 8 or 9. In yet other embodiments, n is independently selected from 6 or 7.

In addition to reaction mixtures comprising additives as described above at their respective concentrations, the invention also provides stock solutions comprising all or some of the above additives, wherein all of the ingredients in the stock solution are 2×, 3×, 5×, 10×, 20×, 25×, 50×, 100×, or another multiple of the above concentrations such that a small amount of the stock solution can be added as a fraction of the total volume of the final reaction mixture. For instance, in some embodiments, a stock solution of an additive as described herein can include a polymerase, nucleotides (e.g., dNTPs) and/or a buffer.

Certain embodiments of the invention provide amplification reaction mixtures that can contain heparin, formalin, tannic acid or any combination thereof. Alternative embodiments provide amplification reaction mixtures in which heparin, formalin and tannic acid are absent.

E. Amplification Reactions Utilizing Compositions of the Invention

As discussed herein, the present invention relates to amplification reactions, including without limitation polymerase chain reaction (PCR), DNA ligase chain reaction (LCR), QBeta RNA replicase, and RNA transcription-based (such as TAS and 3SR) amplification reactions as well as others known to those of skill in the art. Polymerase chain reactions that can be conducted using the compositions described herein include without limitation reverse-transcription PCR (RT-PCR) and quantitative PCR (qPCR) in reaction mixtures.

Amplification reactions, such as polymerase chain reaction (PCR) methods, show an improved efficiency and specificity when compositions of the invention are components of such reactions. Typically, "efficiency" as discussed herein is indicated by the amount of product generated under given reaction conditions. For example, in efficient real-time PCR reactions, the PCR product should double at every cycle. As is known in the art, the efficiency of different kinds of amplification reactions can be calculated using different methods. For example, the exponential amplification of PCR is generally determined using the equation $X_n=X_o*(1+E_x)^n$ (I) where $X_n$ is the number of target molecules at cycle n, $X_o$ is the initial number of target molecules, and $E_x$ is the efficiency of the target amplification and n is the number of cycles. Improvements in efficiency and specificity due to certain aspects of the present invention can be identified and quantified using assays known in the art.

F. Reaction Mixtures

The present invention also provides reaction mixtures comprising one or more of the additives of the invention and at least one of: reverse transcriptase; a polymerase; one or more dNTPs, a biological sample comprising a target nucleic acid. As also discussed herein, the reaction mixtures can contain heparin, formalin, tannic acid or various combinations thereof. Alternative embodiments provide reaction mixtures in which heparin, formalin and tannic acid are absent.

G. Kits

In one aspect, the present invention provides kits for conducting nucleic acid amplification reactions. In some embodiments, such kits include polymerases, and optionally dNTPs, and at least one buffer containing an additive as disclosed herein. The kits may also include one or more primers as well as instructions for conducting nucleic acid amplification reactions using the components of the kits.

In some aspects, instructions included with kits of the invention will include typical amplification protocols that include the following steps: 95-98° C. for about 30 seconds to about 2 minutes 40 cycles (95-98° C. for about 1 to about 5 seconds, 60° C. for about 1 to about 5 seconds, detection step) and a melting cycle at about 60° C. to about 95° C. It will be appreciated that the above exemplary protocol can be varied using parameters well known in the art to optimize nucleic acid amplification reactions to optimize the conditions for efficiency and specificity for different target nucleic acids. For example, amplification of longer target nucleic acids may require longer incubation times and/or higher temperatures for efficient and specific amplification.

H. Nucleotide Bases

Nucleotide bases useful in the present invention can be any nucleotide useful in the polymerization of a nucleic acid. Nucleotides can be naturally occurring, unusual, modified, derivative, or artificial. Nucleotides can be unlabeled, or detectably labeled by methods known in the art (e.g., using radioisotopes, vitamins, fluorescent or chemiluminescent moieties, dioxigenin). Preferably the nucleotides are deoxynucleoside triphosphates, dNTPs (e.g., dATP, dCTP, dGTP, dTTP, dITP, dUTP, α-thio-dNITs, biotin-dUTP, fluorescein-dUTP, digoxigenin-dUTP, 7-deaza-dGTP). dNTPs are also well known in the art and are commercially available from venders (e.g., from Boehringer Mannheim Corp., Indianapolis, Ind.; New England Biolabs, Inc., Beverley, Mass.; Pharmacia LKB Biotechnology, Inc., Piscataway, N.J.).

The nucleotides of the present invention can be present in any concentration. In some embodiments, the nucleotides are present in an amount from about 1 μM to about 1000 μM. In other embodiments, the nucleotides are present in an amount from about 10 μM to about 750 μM. In still other embodiments, the nucleotides are present in an amount from about 100 μM to about 500 μM. One of skill in the art will appreciate that other concentrations of nucleotides are useful in the present invention.

I. Buffering Agents and Salts

Buffering agents and salts useful in the present invention provide appropriate stable pH and ionic conditions for nucleic acid synthesis, e.g., for reverse transcriptase and DNA polymerase activity. A wide variety of buffers and salt solutions and modified buffers are known in the art that can be useful in the present invention, including agents not specifically disclosed herein. Preferred buffering agents include, but are not limited to, TRIS, TRICINE, BIS-TRICINE, HEPES, MOPS, TES, TAPS, PIPES, CAPS. Preferred salt solutions include, but are not limited to, solutions of, potassium acetate, potassium sulfate, potassium chloride, ammonium sulfate, ammonium chloride, ammonium acetate, magnesium chloride, magnesium acetate, magnesium sulfate, manganese chloride, manganese acetate, manganese sulfate, sodium chloride, sodium acetate, lithium chloride, and lithium acetate.

The buffering agents of the present invention can be present in any concentration. In some embodiments, the buffering agent is present in an amount from about 0.1 mM to about 1000 mM. In other embodiments, the buffer is present in an amount from about 1 mM to about 500 mM. In still other embodiments, the buffer is present in an amount from about 5 mM to about 250 mM. One of skill in the art will appreciate that other concentrations of buffer are useful in the present invention.

Various non-limiting embodiments include:
1. A reaction mixture comprising a reverse transcriptase and one or more additive selected from glutamate or salts thereof, poloxamer 188, histidine or salts thereof and polyvinyl sulfonic acid (PVSA) and one or more oligonucleotides selected from: $X_1$-$X_2$-$X_3$-$X_4$-$X_5$, $X_1$-$X_2$-$X_3$-$X_4$-$X_5$-$X_6$, $X_1$-$X_2$-$X_3$-$X_4$-$X_5$-$X_6$-$X_7$, $X_1$-$X_2$-$X_3$-$X_4$-$X_5$-$X_6$-$X_7$-$X_8$, $X_1$-$X_2$-$X_3$-$X_4$-$X_5$-$X_6$-$X_7$-$X_8$-$X_9$, $X_1$-$X_2$-$X_3$-$X_4$-$X_5$-$X_6$-$X_7$-$X_8$-$X_9$-$X_{10}$ (SEQ ID NO: 21), $X_1$-$X_2$-$X_3$-$X_4$-$X_5$-$X_6$-$X_7$-$X_8$-$X_9$-$X_{10}$-$X_{11}$ (SEQ ID NO: 22), or $X_1$-$X_2$-$X_3$-$X_4$-$X_5$-$X_6$-$X_7$-$X_8$-$X_9$-$X_{10}$-$X_{11}$-$X_{12}$ (SEQ ID NO: 23.
2. The reaction mixture of embodiment 1, wherein the additive is: a) glutamate or a salt thereof; b) histidine or a salt thereof; c) poloxamer 188; d) PVSA; e) glutamate or a salt thereof and histidine or a salt thereof; f) glutamate or a salt thereof and poloxamer 188; g) glutamate or a salt thereof and PVSA; h) histidine or a salt thereof and poloxamer 188; i) histidine or a salt thereof and PVSA; j) poloxamer 188 and PVSA; k) glutamate or a salt thereof, histidine or a salt thereof and poloxamer 188; l) glutamate or a salt thereof, histidine or a salt thereof and PVSA; m) histidine or a salt thereof, poloxamer 188 and PVSA; n) glutamate or a salt thereof, histidine or a salt thereof, poloxamer 188 and PVSA; or o) glutamate or a salt thereof, poloxamer 188 and PVSA.
3. The reaction mixture of embodiment 1 or 2, wherein the glutamate salt is potassium glutamate and the histidine salt is histidine HCl monohydrate.
4. The reaction mixture of any one of embodiments 1-3, wherein:
a) the poloxamer is present in an amount (v/v %) ranging from about 0.01% to about 5%;
b) histidine or a salt thereof is present in a concentration of about 1 mM to about 50 mM, about 5 mM to about 40 mM, about 2.5 mM to about 30 mM, about 5 mM to about 30 mM, about 10 mM to about 30 mM, about 10 mM to about 25 mM, or about 15 mM to about 20 mM;
c) glutamate or a salt thereof is present in a concentration of about 5 mM to about 250 mM, about 10 mM to about 400 mM, about 10 mM to about 300 mM, about 10 mM to about 250 mM, about 10 mM to about 200 mM, about 10 mM to about 150 mM, about 15 mM to about 400 mM, about 15 mM to about 300 mM, about 15 mM to about 250 mM, about 15 mM to about 200 mM or about 15 mM to about 150 mM; and/or
d) PVSA is present in an amount (v/v %) of about 0.0001% to about 0.002%, about 0.0001% to about 0.005%, about 0.0001% to about 0.004%, about 0.0001% to about 0.003%, about 0.0001% to about 0.002%, or about 0.0001% to about 0.001%.
5. The reaction mixture of embodiment 1, wherein the additive is one or more oligonucleotides.
6. The reaction mixture of embodiment 5, said one or more oligonucleotides containing one or more phosphorothioate bonds at any position within said one or more oligonucleotide.
7. The reaction mixture of embodiment 6, said one or more oligonucleotides contain one or more phosphorothioate bond between the ultimate, penultimate and/or antepenultimate nucleotides at the 5' end, the 3' end or both the 5' and 3' ends of the oligonucleotide.
8. The reaction mixture of embodiment 1, 5, 6 or 7, wherein said one or more oligonucleotides is a random sequence of nucleotides selected from A, G, T and C.
9. The reaction mixture of embodiment 1, 5, 6, 7 or 8, wherein said one or more oligonucleotides is an:
a) $X_1$-$X_2$-$X_3$-$X_4$-$X_5$ oligonucleotide sequence that is: i) randomly ordered A and T nucleotides; ii) randomly ordered G and C nucleotides; iii) at least one but less than five of the nucleotides are randomly selected from a group consisting of: A, G, T, and C, while the remaining nucleotides are randomly selected G and C nucleotides; or iv) at least one but less than five of the nucleotides are randomly selected from a group consisting of: A, G, T, and C, while the remaining nucleotides are randomly selected A and T nucleotides;
b) $X_1$-$X_2$-$X_3$-$X_4$-$X_5$-$X_6$ oligonucleotide sequence that is: i) randomly ordered A and T nucleotides; ii) randomly ordered G and C nucleotides; iii) at least one but less than six of the nucleotides are randomly selected from a group consisting of: A, G, T, and C, while the remaining nucleotides are randomly selected G and C nucleotides; or iv) at least one but less than six of the nucleotides are randomly selected from a group consisting of: A, G, T, and C, while the remaining nucleotides are randomly selected A and T nucleotides;
c) $X_1$-$X_2$-$X_3$-$X_4$-$X_5$-$X_6$-$X_7$ oligonucleotide sequence that is: i) randomly ordered A and T nucleotides; ii) randomly ordered G and C nucleotides; iii) at least one but less than seven of the nucleotides are randomly selected from a group consisting of: A, G, T, and C, while the remaining nucleotides are randomly selected G and C nucleotides; or iv) at least one but less than seven of the nucleotides are randomly selected from a group consisting of: A, G, T, and C, while the remaining nucleotides are randomly selected A and T nucleotides;
d) $X_1$-$X_2$-$X_3$-$X_4$-$X_5$-$X_6$-$X_7$-$X_8$ oligonucleotide sequence that is: i) randomly ordered A and T nucleotides; ii) randomly ordered G and C nucleotides; iii) at least one but less than eight of the nucleotides are randomly selected from a group consisting of: A, G, T, and C, while the remaining nucleotides are randomly selected G and C nucleotides; or iv) at least one but less than eight of the nucleotides are randomly selected from a group consisting of: A, G, T, and C, while the remaining nucleotides are randomly selected A and T nucleotides;
e) $X_1$-$X_2$-$X_3$-$X_4$-$X_5$-$X_6$-$X_7$-$X_8$-$X_9$ oligonucleotide sequence that is: i) randomly ordered A and T nucleotides; ii) randomly ordered G and C nucleotides; iii) at least one but less than nine of the nucleotides are randomly selected from a group consisting of: A, G, T, and C, while the remaining nucleotides are randomly selected G and C nucleotides; or iv) at least one but less than nine of the nucleotides are randomly selected from a group consisting of: A, G, T, and C, while the remaining nucleotides are randomly selected A and T nucleotides;
f) $X_1$-$X_2$-$X_3$-$X_4$-$X_5$-$X_6$-$X_7$-$X_8$-$X_9$-$X_{10}$ (SEQ ID NO: 21) oligonucleotide sequence that is: i) randomly ordered A and T nucleotides; ii) randomly ordered G and C nucleotides; iii) at least one but less than ten of the nucleotides are randomly selected from a group consisting of: A, G, T, and C, while the remaining nucleotides are randomly selected G and C nucleotides; or iv) at least one but less than ten of the nucleotides are randomly selected from a group consisting of: A, G, T, and C, while the remaining nucleotides are randomly selected A and T nucleotides;
g) $X_1$-$X_2$-$X_3$-$X_4$-$X_5$-$X_6$-$X_7$-$X_8$-$X_9$-$X_{10}$-$X_{11}$ (SEQ ID NO: 22) oligonucleotide sequence that is: i) randomly ordered A and T nucleotides; ii) randomly ordered G and C nucleotides; iii) at least one but less than eleven of the nucleotides are randomly selected from a group consisting of: A, G, T, and C, while the remaining nucleotides are randomly selected G and C nucleotides; or iv) at least one but less than eleven of the nucleotides are randomly selected from a group consisting of: A, G, T, and C, while the remaining nucleotides are randomly selected A and T nucleotides; or h) $X_1$-$X_2$-$X_3$-$X_4$-$X_5$-$X_6$-$X_7$-$X_8$-$X_9$-$X_{10}$-$X_{11}$-$X_{12}$ (SEQ ID NO: 23) oligonucleotide sequence that is: i) randomly ordered A and T nucleotides; ii) randomly ordered G and C nucleotides; iii) at least one but less than twelve of the nucleotides are randomly selected from a group consisting of: A, G, T, and C, while the remaining nucleotides are randomly selected G and C nucleotides; or iv) at least one but less than twelve of the nucleotides are randomly selected from a group consisting of: A, G, T, and C, while the remaining nucleotides are randomly selected A and T nucleotides.

10. The reaction mixture of embodiment 1, 5, 6, 7, 8 or 9, wherein the oligonucleotide has high GC content and at least 60% of the nucleotides are G and/or C or the oligonucleotide has high AT content and at least 60% of the nucleotides are A and/or T.

11. The reaction mixture of embodiment 2, 3 or 4, wherein the reaction mixture further comprises one or more oligonucleotides as an additive.

12. The reaction mixture of embodiment 11, said one or more oligonucleotide containing one or more phosphorothioate bonds at any position within the oligonucleotide.

13. The reaction mixture of embodiment 12, said one or more oligonucleotides contain one or more phosphorothioate bond between the ultimate, penultimate and/or antepenultimate nucleotides at the 5' end, the 3' end or both the 5' and 3' ends of the oligonucleotide.

14. The reaction mixture of embodiment 11, 12 or 13, wherein said one or more oligonucleotides are random sequences of nucleotides selected from A, G, T and C.

15. The reaction mixture of embodiment 11, 12 or 13, wherein said one or more oligonucleotide is an:

a) $X_1$-$X_2$-$X_3$-$X_4$-$X_5$ oligonucleotide sequence that is: i) randomly ordered A and T nucleotides; ii) randomly ordered G and C nucleotides; iii) at least one but less than five of the nucleotides are randomly selected from a group consisting of: A, G, T, and C, while the remaining nucleotides are randomly selected G and C nucleotides; or iv) at least one but less than five of the nucleotides are randomly selected from a group consisting of: A, G, T, and C, while the remaining nucleotides are randomly selected A and T nucleotides;

b) $X_1$-$X_2$-$X_3$-$X_4$-$X_5$-$X_6$ oligonucleotide sequence that is: i) randomly ordered A and T nucleotides; ii) randomly ordered G and C nucleotides; iii) at least one but less than six of the nucleotides are randomly selected from a group consisting of: A, G, T, and C, while the remaining nucleotides are randomly selected G and C nucleotides; or iv) at least one but less than six of the nucleotides are randomly selected from a group consisting of: A, G, T, and C, while the remaining nucleotides are randomly selected A and T nucleotides;

c) $X_1$-$X_2$-$X_3$-$X_4$-$X_5$-$X_6$-$X_7$ oligonucleotide sequence that is: i) randomly ordered A and T nucleotides; ii) randomly ordered G and C nucleotides; iii) at least one but less than seven of the nucleotides are randomly selected from a group consisting of: A, G, T, and C, while the remaining nucleotides are randomly selected G and C nucleotides; or iv) at least one but less than seven of the nucleotides are randomly selected from a group consisting of: A, G, T, and C, while the remaining nucleotides are randomly selected A and T nucleotides;

d) $X_1$-$X_2$-$X_3$-$X_4$-$X_5$-$X_6$-$X_7$-$X_8$ oligonucleotide sequence that is: i) randomly ordered A and T nucleotides; ii) randomly ordered G and C nucleotides; iii) at least one but less than eight of the nucleotides are randomly selected from a group consisting of: A, G, T, and C, while the remaining nucleotides are randomly selected G and C nucleotides; or iv) at least one but less than eight of the nucleotides are randomly selected from a group consisting of: A, G, T, and C, while the remaining nucleotides are randomly selected A and T nucleotides;

e) $X_1$-$X_2$-$X_3$-$X_4$-$X_5$-$X_6$-$X_7$-$X_8$-$X_9$ oligonucleotide sequence that is: i) randomly ordered A and T nucleotides; ii) randomly ordered G and C nucleotides; iii) at least one but less than nine of the nucleotides are randomly selected from a group consisting of: A, G, T, and C, while the remaining nucleotides are randomly selected G and C nucleotides; or iv) at least one but less than nine of the nucleotides are randomly selected from a group consisting of: A, G, T, and C, while the remaining nucleotides are randomly selected A and T nucleotides;

f) $X_1$-$X_2$-$X_3$-$X_4$-$X_5$-$X_6$-$X_7$-$X_8$-$X_9$-$X_{10}$ (SEQ ID NO: 21) oligonucleotide sequence that is: i) randomly ordered A and T nucleotides; ii) randomly ordered G and C nucleotides; iii) at least one but less than ten of the nucleotides are randomly selected from a group consisting of: A, G, T, and C, while the remaining nucleotides are randomly selected G and C nucleotides; or iv) at least one but less than ten of the nucleotides are randomly selected from a group consisting of: A, G, T, and C, while the remaining nucleotides are randomly selected A and T nucleotides;

g) $X_1$-$X_2$-$X_3$-$X_4$-$X_5$-$X_6$-$X_7$-$X_8$-$X_9$-$X_{10}$-$X_{11}$ (SEQ ID NO: 22) oligonucleotide sequence that is: i) randomly ordered A and T nucleotides; ii) randomly ordered G and C nucleotides; iii) at least one but less than eleven of the nucleotides are randomly selected from a group consisting of: A, G, T, and C, while the remaining nucleotides are randomly selected G and C nucleotides; or iv) at least one but less than eleven of the nucleotides are randomly selected from a group consisting of: A, G, T, and C, while the remaining nucleotides are randomly selected A and T nucleotides; or h) $X_1$-$X_2$-$X_3$-$X_4$-$X_5$-$X_6$-$X_7$-$X_8$-$X_9$-$X_{10}$-$X_{11}$-$X_{12}$ (SEQ ID NO: 23) oligonucleotide sequence that is: i) randomly ordered A and T nucleotides; ii) randomly ordered G and C nucleotides; iii) at least one but less than twelve of the nucleotides are randomly selected from a group consisting of: A, G, T, and C, while the remaining nucleotides are randomly selected G and C nucleotides; or iv) at least one but less than twelve of the nucleotides are randomly selected from a group consisting of: A, G, T, and C, while the remaining nucleotides are randomly selected A and T nucleotides.

16. The reaction mixture of embodiments 11-15, wherein one or more of said oligonucleotides has high GC content and at least 60% of the nucleotides are G and/or C or said one or more oligonucleotides has high AT content and at least 60% of the nucleotides are A and/or T.

17. The reaction mixture of any one of embodiments 1 or 5-16, wherein said one or more oligonucleotide is selected from $dW_n$, where W is A or T and n is an integer selected from 5, 6, 7, 8, 9, 10, 11 or 12, $dS_n$, where S is G or C and n is an integer selected from 5, 6, 7, 8, 9, 10, 11 or 12, $dA_n$ where n is an integer selected from 5, 6, 7, 8, 9, 10, 11 or 12, $dG_n$, where n is an integer selected from 5, 6, 7, 8, 9, 10, 11 or 12, $dC_n$, where n is an integer selected from 5, 6, 7, 8, 9, 10, 11 or 12, $dT_n$, where n is an integer selected from 5, 6, 7, 8, 9, 10, 11 or 12 or any combination of $dW_n$, $dS_n$, $dA_n$, $dG_n$ $dC_n$, and $dT_n$.

18. The reaction mixture of embodiment 17, wherein the concentration of said any one or more oligonucleotides is 0.1 µM and about 1000 µM, about 2.5 µM and about 750 µM, about 5 µM and about 500 µM, about 5 µM and about 250 µM, about 5 µM and about 100 µM, about 10 µM and about 500 µM, about 10 µM and about 250 µM, about 10 µM and about 100 µM or about 10 µM and about 50 µM.

19. The reaction mixture of any preceding embodiment, wherein the reaction mixture contains one or more of the following RT inhibitors: heparin, formalin and/or tannic acid.

20. The reaction mixture of any one of embodiments 1-18, wherein said reaction mixture does not contain heparin, formalin and/or tannic acid.

21. A method of reducing the inhibition of reverse transcriptase by formalin, wherein the method comprises the addition of an RNA template to a reaction mixture according to any one of embodiments 1-19, incubating the mixture, and synthesizing complementary DNA to a portion of or the entire template RNA, said reaction mixture comprising formalin and at least histidine and/or a salt thereof as an additive.

22. A method of reducing the inhibition of reverse transcriptase by heparin, wherein the method comprises the addition of an RNA template to a reaction mixture of any one of embodiments 1-19, incubating the mixture, and synthesizing complementary DNA to a portion of or the entire template RNA, said reaction mixture comprising heparin and at least histidine and/or salts thereof and/or glutamate and/or salts thereof as an additive.

23. A method of reducing the inhibition of reverse transcriptase by tannic acid, wherein the method comprises the addition of an RNA template to a reaction mixture of any one of embodiments 1-19, incubating the mixture, and synthesizing complementary DNA to a portion of or the entire template RNA, said reaction mixture comprising tannic acid and at least poloxamer 188 as an additive.

24. A method of improving the efficiency and sensitivity of reverse transcriptase, wherein the method comprises of the addition of an RNA template to a reaction mixture of any one of embodiments 1-19 and incubating the mixture to synthesize complementary DNA to all or a portion of the template RNA, said reaction mixture comprising PVSA as an additive.

25. A method of enhancing reverse transcriptase activity, wherein the method comprises of the addition of an RNA template to a reaction mixture and incubating the mixture to synthesize complementary DNA to all or a portion of the template RNA, said reaction mixture containing one or more oligonucleotide as defined in any one of embodiments 5-10 as an additive.

26. The method of embodiment 25, wherein said one or more oligonucleotide is a combination of oligonucleotides selected from:
a) $RX_n$ and $dW_n$;
b) $RX_n$ and $dS_n$;
c) $RX_n$, $dW_n$ and $dS_n$;
d) $RX_n$ and $dT_n$;
e) $RX_n$, $dT_n$ and $dS_n$; or
f) $RX_n$, $dT_n$, $dW_n$ and $dS_n$.
wherein each n for a given oligonucleotide is independently selected from an integer selected from 5, 6, 7, 8, 9, 10, 11 or 12.

27. The method of embodiment 26, wherein each n is independently selected from 5, 6, 7, 8 or 9 for each oligonucleotide. In yet other embodiments, n is independently selected from 6 or 7.

28. The method of embodiment 27, wherein each n is independently selected from 6 or 7 for each oligonucleotide.

29. The method of any one of embodiments 25-28, said reaction further comprising an additive according to any one of embodiments 1-4.

30. The method of any one of embodiments 25-28, said one or more oligonucleotide contains one or more phosphorothioate bonds at any position within said one or more oligonucleotide.

31. The method of embodiment 30, wherein said one or more oligonucleotide contains one or more phosphorothioate bond between the ultimate, penultimate and/or antepenultimate nucleotides at the 5' end, the 3' end or both the 5' and 3' ends of the oligonucleotide.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Example 1. An Exemplary RT-qPCR Mix

An RT reaction buffer was formulated so that the RT reaction can be carried out after being mixed together with thermo-stable RT (e.g., MMLV or engineered MMLV) and RNA templates (e.g., Hela RNA). In a 20 µl RT reaction mix there is 1 u of RT enzyme, 10 u of Rnasin (Rnase inhibitor), nucleotides each at 1.5 mM (e.g., dATP, dCTP, dGTP, dTTP), random hexamer, oligo dT, or gene-specific oligo nucleotides at appropriate concentration (0.5 to 1 uM), 4% glycerol, 0.01% detergent (e.g., Tween 20), with or without RT inhibitors (e.g., Heparin, Ethanol, Guanidine Hydrochloride, Formalin, Tannic acid, etc.) or additives that improve RT reaction efficiency or sensitivity (e.g., PVSA). The RT reaction was completed in a T100 Thermo Cycler (Bio-Rad Laboratories Inc. Hercules, Calif.). The RT reaction protocol was as follows: 50° C. 20 min, 95° C. 1 min, and incubation at 4° C.

After RT reaction, the RT products were used for qPCR reaction using SsoAdvanced Universal SYBR Green Supermix (Bio-Rad Laboratories Inc. Hercules, Calif.). The RT product inputs in qPCR reaction ranged from 10% to 0.1% of qPCR reaction, depending on the expression abundance of target genes. Target gene primers (Table 3) at 250 nM were used. The following protocol of qPCR was used on CFC348 Thermo Cycler (Bio-Rad Laboratories Inc. Hercules, Calif.): 95° C. denaturation for 2 min, 40 cycles of 95° C. 5S denaturation, 60° C. 30S annealing/extension/read. After qPCR reaction, Cq values from RT products with and without inhibitors were compared, and usually Cq values were delayed (bigger values) when inhibitors were present.

The larger the Cq value relative to no inhibitor RT products, the more inhibition of RT reaction observed.

Example 2. The Effect of K-Glu on Heparin Tolerance

When inhibitor Heparin (Sigma, H3149) was added in RT reaction at 0.0034 u/μl, qPCR from the RT products were greatly delayed compared with the RT products without heparin. Both GAPDH and 18S showed similar results. When 100 mM of potassium Glutamate (Sigma, C1149) was added in the RT reaction with heparin, the qPCR results from the RT products did not show much delay compared to the RT products without heparin. This indicated that the potassium glutamate in RT reaction improved its tolerance to heparin. Other salts (e.g., $(NH_4)_2SO_4$) may also improve Heparin tolerance, but they may compromise other inhibitor tolerance (e.g., Ethanol, Guanidine Hydrochloride, Calbiochem, 369075).

Example 3. Effect of Poloxamer on Tannic Acid Tolerance

When inhibitor tannic acid (Sigma, 403040) was added in RT reaction at 0.1 μg/μl, qPCR results from the RT products were greatly delayed compared with the RT products without tannic acid. Human GAPDH target gene was detected in the qPCR reaction. When 0.5% Poloxamer (Sigma, P5556) was added in the RT reaction with the same concentration of tannic acid, the qPCR results from the RT products did not show much delay compared to the RT products without tannic acid. This indicated that poloxamer effectively improves RT tolerance to tannic acid.

Example 4. Effect of His-HCl on Formalin Tolerance

When inhibitor Formalin (EMD, R04586-76) was added in RT reaction at 0.125%, qPCR results from the RT products were significantly delayed compared with the RT products without formalin. Human GAPDH target gene was detected in the qPCR reaction. When 15 to 20 mM His-HCl (Sigma, H8125) was added in the RT reaction with the same concentration of formalin, the qPCR results from the RT products did not show a lot delay compared to the RT products without formalin. This indicated that His-HCl effectively improves RT tolerance to formalin.

Example 5. Effect of PVSA (Polyvinyl Sulfonic Acid) on RT Yield and Sensitivity When RNA inputs in RT reaction are limited (low input of RNA template) and there was no PVSA (Sigma, 278424), qPCR results from the RT products were significantly delayed compared to the RT products with 0.0003% PVSA. Human GAPDH target gene was detected in the qPCR reaction.

Example 6. Enhancement in Reverse Transcription of the High and Low GC Targets In the RT reaction when low/high GC random primers were supplemented, qPCR results from the RT products were significantly improved (earlier Cq, smaller Cq values) compared to the RT products without supplementation of low/high GC for low or high GC targets (Target genes in table 3).

TABLE 1

Enhancement in reverse transcription of the high and low GC targets.
Reverse Transcription was carried out using random hexamers only or supplemented with different low/high GC random primers. The cDNA was quantified by qPCR. dCq was calculated between conditions using random primers only in reverse transcription and those supplemented with low/high GC random primers; dCq (-Cq(RH)-Cq (test condition). A negative dCq value indicates earlier Cq for the test condition and enhanced reverse transcription.

|  | RH | RH/dW6 (10 uM) | RH/dW7 (10 uM) | RH/dS6 (10 uM) | RH/dS7 (10 uM) | RH/dW6/dS6 (5 + 5) | RH/dW6/dS7 (5 + 5) | RH/dW7/dS6 (5 + 5) | RH/dW7/dS7 (5 + 5) | RH/dT6 (10 uM) | RH/dT6/dS6 (10 + 10) | RH/dT6/dW7/dS6 (10 + 10 + 10) |
|---|---|---|---|---|---|---|---|---|---|---|---|---|
|  |  |  |  |  |  | Cq |  |  |  |  |  |  |
| NGFRP198 | 23.05 | 22.23 | 21.46 | 22.59 | 22.97 | 23.11 | 23.03 | 22.59 | 22.82 | 21.54 | 21.61 | 21.48 |
| SNRPE109 | 21.54 | 21.12 | 20.49 | 21.18 | 21.31 | 21.77 | 21.75 | 21.52 | 21.63 | 20.64 | 20.61 | 20.44 |
| TXN192 | 28.31 | 27.62 | 26.87 | 28.03 | 27.95 | 28.28 | 28.16 | 27.80 | 28.03 | 26.59 | 26.67 | 26.69 |
| RHPN2 | 27.62 | 27.36 | 26.44 | 27.04 | 26.94 | 26.90 | 27.18 | 27.46 | 27.24 | 26.15 | 27.83 | 26.50 |
| SBNO2 GC3 | 24.64 | 24.47 | 24.37 | 24.27 | 24.18 | 24.40 | 24.49 | 24.56 | 24.58 | 24.93 | 24.74 | 24.54 |
| CBP hgc1 | 28.08 | 27.68 | 27.80 | 27.47 | 27.33 | 27.67 | 27.91 | 27.74 | 27.95 | 28.27 | 27.85 | 27.60 |
| CBP hgc2 | 28.57 | 28.26 | 28.15 | 27.80 | 28.00 | 28.54 | 28.42 | 28.48 | 28.47 | 28.84 | 28.27 | 28.22 |
| CBP hgc3 | 28.03 | 27.40 | 27.39 | 27.00 | 27.06 | 27.44 | 27.45 | 27.36 | 27.48 | 28.02 | 27.14 | 27.08 |
|  |  |  |  |  |  | dCq |  |  |  |  |  |  |
| NGFRP198 | 0.00 | −0.82 * | −1.59 ** | −0.46 | −0.08 | −0.49 | −0.57 * | −1.01 ** | −0.78 * | −1.95 ** | −1.87 ** | −2.01 ** |
| SNRPE109 | 0.00 | −0.42 | −1.04 ** | −0.36 | −0.23 | −0.41 | −0.43 | −0.66 * | −0.55 * | −0.93 ** | −0.96 ** | −1.13 ** |
| TXN192 | 0.00 | −0.69 * | −1.44 ** | −0.28 | −0.36 | −0.42 | −0.53 * | −0.90 * | −0.67 * | −1.63 ** | −1.55 ** | −1.53 ** |
| RHPN2 | 0.00 | −0.26 | −1.18 ** | −0.58 * | −0.68 * | −2.32 ** | −2.03 ** | −1.76 ** | −1.98 ** | −1.39 ** | 0.29 | −1.04 ** |
| SBNO2 GC3 | 0.00 | −0.17 | −0.27 | −0.37 | −0.45 | −0.53 * | −0.44 | −0.37 | −0.35 | −0.26 | −0.44 | −0.65 * |
| CBP hgc1 | 0.00 | −0.40 | −0.28 | −0.62 * | −0.75 * | −0.75 * | −0.50 * | −0.67 * | −0.47 | −0.26 | −0.67 * | −0.93 ** |
| CBP hgc2 | 0.00 | −0.31 | −0.42 | −0.77 * | −0.56 * | −0.36 | −0.48 | −0.42 | −0.43 | 0.07 | −0.51 | −0.55 * |
| CBP hgc3 | 0.00 | −0.63 * | 0.64 * | −1.03 ** | −0.97 ** | −0.53 * | −0.52 * | −0.61 * | −0.49 | −0.06 | −0.94 ** | −0.99 ** |

RH: DNA random hexamer; dW7; oligo dW septamer; dS6; oligo dS hexamer. dT6: oligo dT hexamer. Oligo concentrations used are indicated.
* −0.5 ≥ dCq ≥ −0.9; ** dCq ≤ −0.91.

TABLE 2

The GC content of different RNA targets

| | GC content (%) |
|---|---|
| NGFRAP198 | 40 |
| SNRPE109 | 35.8 |
| TXN192 | 29 |
| RHPN2 | 27 |
| SBNO2 GC3 | 74.8 |
| CBP hgc1 | 78.5 |
| CBP hgc2 | 81.7 |
| CBP hgc3 | 78.3 |

TABLE 3

Primer sequences used in the study of this application

| Human Genes | Amplicon length (bp) | Forward primers | Reverse primers |
|---|---|---|---|
| GAPDH | 226 | GAAGGTGAAGGTCGGAGTC (SEQ ID NO: 1) | GAAGATGGTGATGGGATTTC (SEQ ID NO: 2) |
| 18S | 102 | AGGAATTCCCAGTAAGTGCG (SEQ ID NO: 3) | GCCTCACTAAACCATCCAA (SEQ ID NO: 4) |
| NGFRAP | 198 | AGCTCTCTAATCACCATGAC (SEQ ID NO: 5) | AATAGAAGCTGGCAACACAA (SEQ ID NO: 6) |
| SNRPE | 109 | TGATGCAGAAGAGATTCATTCTAA (SEQ ID NO: 7) | TCATTTCTAGTTGGAGACACT (SEQ ID NO: 8) |
| TXN | 192 | ATTCAGACATGAGACGGTTT (SEQ ID NO: 9) | AAAGCTTGAAGCCACCATTA (SEQ ID NO: 10) |
| RHPN2 | 119 | GCCATATTTCATATCTTCAACACT (SEQ ID NO: 11) | AGAAACCTCTAGGAATTAGTGA (SEQ ID NO: 12) |
| SBNO2GC3 | 119 | GAAGTTGATGTCGCAGCCCT (SEQ ID NO: 13) | ACTTCTCTTTCCCGGCGC (SEQ ID NO: 14) |
| CBP hgc1 | 195 | GTTGCTGTGGCTGAGATTTGG (SEQ ID NO: 15) | CATTTTCACCTGCTCGCGAA (SEQ ID NO: 16) |
| CBP hgc2 | 175 | GTTGCTGTGGCTGAGATTTGG (SEQ ID NO: 17) | AACAGCCCCGGGCAC (SEQ ID NO: 18) |
| CBP hgc3 | 106 | GTTGCTGTGGCTGAGATTTGG (SEQ ID NO: 19) | AGGGAGAGGAGCGAGC (SEQ ID NO: 20) |

We claim:

1. A composition comprising: oligonucleotide $dG_n$ or oligonucleotide $dC_n$ and n is an integer selected from 5, 6, 7, 8, 9, 10, 11 or 12, oligonucleotide $dT_n$, where n is an integer selected from 5, 6, 7, 8, 9, 10, 11 or 12, glutamate or a salt thereof, poloxamer 188, polyvinyl sulfonic acid (PVSA), and one or more oligonucleotides selected from: $X_1$-$X_2$-$X_3$-$X_4$-$X_5$, $X_1$-$X_2$-$X_3$-$X_4$-$X_5$-$X_6$, $X_1$-$X_2$-$X_3$-$X_4$-$X_5$-$X_6$-$X_7$, $X_1$-$X_2$-$X_3$-$X_4$-$X_5$-$X_6$-$X_7$-$X_8$, $X_1$-$X_2$-$X_3$-$X_4$-$X_5$-$X_6$-$X_7$-$X_8$-$X_9$, $X_1$-$X_2$-$X_3$-$X_4$-$X_5$-$X_6$-$X_7$-$X_8$-$X_9$-$X_{10}$ (SEQ ID NO: 21), $X_1$-$X_2$-$X_3$-$X_4$-$X_5$-$X_6$-$X_7$-$X_8$-$X_9$-$X_{10}$-$X_{11}$ (SEQ ID NO: 22), and $X_1$-$X_2$-$X_3$-$X_4$-$X_5$-$X_6$-$X_7$-$X_8$-$X_9$-$X_{10}$-$X_{11}$-$X_{12}$ (SEQ ID NO: 23), and wherein:

$X_1$-$X_2$-$X_3$-$X_4$-$X_5$ are: i) randomly ordered A and T nucleotides; ii) randomly ordered G and C nucleotides; or iii) at least one but less than five of the nucleotides are randomly selected from the group consisting of: A and T, while the remaining nucleotides are randomly selected G and C nucleotides;

$X_1$-$X_2$-$X_3$-$X_4$-$X_5$-$X_6$ are: i) randomly ordered A and T nucleotides; ii) randomly ordered G and C nucleotides; or iii) at least one but less than six of the nucleotides are randomly selected from the group consisting of: A and T, while the remaining nucleotides are randomly selected G and C nucleotides;

$X_1$-$X_2$-$X_3$-$X_4$-$X_5$-$X_6$-$X_7$ are: i) randomly ordered A and T nucleotides; ii) randomly ordered G and C nucleotides; or iii) at least one but less than seven of the nucleotides are randomly selected from the group consisting of: A and T, while the remaining nucleotides are randomly selected G and C nucleotides;

$X_1$-$X_2$-$X_3$-$X_4$-$X_5$-$X_6$-$X_7$-$X_8$ are: i) randomly ordered A and T nucleotides; ii) randomly ordered G and C nucleotides; or iii) at least one but less than eight of the nucleotides are randomly selected from the group consisting of: A and T, while the remaining nucleotides are randomly selected G and C nucleotides;

$X_1$-$X_2$-$X_3$-$X_4$-$X_5$-$X_6$-$X_7$-$X_8$-$X_9$ are: i) randomly ordered A and T nucleotides; ii) randomly ordered G and C nucleotides; or iii) at least one but less than nine of the nucleotides are randomly selected from the group consisting of: A and T, while the remaining nucleotides are randomly selected G and C nucleotides;

$X_1$-$X_2$-$X_3$-$X_4$-$X_5$-$X_6$-$X_7$-$X_8$-$X_9$-$X_{10}$ (SEQ ID NO: 21) are: i) randomly ordered A and T nucleotides; ii) randomly ordered G and C nucleotides; or iii) at least one but less than ten of the nucleotides are randomly selected from the group consisting of: A and T, while the remaining nucleotides are randomly selected G and C nucleotides;

$X_1$-$X_2$-$X_3$-$X_4$-$X_5$-$X_6$-$X_7$-$X_8$-$X_9$-$X_{10}$-$X_{11}$ (SEQ ID NO: 22) are: i) randomly ordered A and T nucleotides; ii) randomly ordered G and C nucleotides; or iii) at least one but less than eleven of the nucleotides are randomly selected from the group consisting of: A and T, while the remaining nucleotides are randomly selected G and C nucleotides; and $X_1$-$X_2$-$X_3$-$X_4$-$X_5$-$X_6$-$X_7$-$X_8$-$X_9$-$X_{10}$-$X_{11}$-$X_{12}$ (SEQ ID NO: 23) are: i) randomly ordered A and T nucleotides; ii) randomly ordered G and C nucleotides; or iii) at least one but less than twelve of the nucleotides are randomly selected from the group consisting of: A and T, while the remaining nucleotides are randomly selected G and C nucleotides.

2. The composition of claim 1, wherein the glutamate salt is potassium glutamate.

3. The composition of claim 1, wherein:
a) the poloxamer is present in an amount (v/v %) ranging from about 0.01% to about 5%;
b) glutamate or a salt thereof is present in a concentration of about 5 mM to about 250 mM; and
c) PVSA is present in an amount (v/v %) of about 0.0001% to about 0.002%.

4. The composition of claim 1, said one or more oligonucleotides containing one or more phosphorothioate bonds at any position within said one or more oligonucleotide, said one or more oligonucleotides being selected from: $X_1$-$X_2$-$X_3$-$X_4$-$X_5$, $X_1$-$X_2$-$X_3$-$X_4$-$X_5$-$X_6$, $X_1$-$X_2$-$X_3$-$X_4$-$X_5$-$X_6$-$X_7$, $X_1$-$X_2$-$X_3$-$X_4$-$X_5$-$X_6$-$X_7$-$X_8$, $X_1$-$X_2$-$X_3$-$X_4$-$X_5$-$X_6$-$X_7$-$X_8$-$X_9$, $X_1$-$X_2$-$X_3$-$X_4$-$X_5$-$X_6$-$X_7$-$X_8$-$X_9$-$X_{10}$ (SEQ ID NO: 21), $X_1$-$X_2$-$X_3$-$X_4$-$X_5$-$X_6$-$X_7$-$X_8$-$X_9$-$X_{10}$-$X_{11}$ (SEQ ID NO: 22), and $X_1$-$X_2$-$X_3$-$X_4$-$X_5$-$X_6$-$X_7$-$X_8$-$X_9$-$X_{10}$-$X_{11}$-$X_{12}$ (SEQ ID NO: 23).

5. The composition of claim 4, wherein said one or more oligonucleotides contain one or more phosphorothioate bond between the ultimate, penultimate and/or antepenultimate nucleotides at the 5' end, the 3' end or both the 5' and 3' ends of the oligonucleotide.

6. The composition of claim 1, wherein said oligonucleotide $dG_n$ or oligonucleotide $dC_n$ and/or said oligonucleotide dTn contain one or more phosphorothioate bonds at any position within the oligonucleotide.

7. The composition of claim 6, wherein said oligonucleotide $dG_n$ or oligonucleotide $dC_n$ and/or said oligonucleotide dTn containing one or more phosphorothioate bond between the ultimate, penultimate and/or antepenultimate nucleotides at the 5' end, the 3' end or both the 5' and 3' ends of the oligonucleotide.

8. The composition of claim 1, wherein the concentration of said oligonucleotide $dG_n$ or oligonucleotide $dC_n$ and/or said oligonucleotide dTn is between 0.1 µM and about 1000 µM.

9. The composition of claim 1, wherein the composition further comprises a reverse transcriptase and one or more of the following RT inhibitors: heparin, formalin and/or tannic acid.

10. The composition of claim 1, wherein said composition further comprises a reverse transcriptase and does not contain heparin, formalin and/or tannic acid.

11. The composition of claim 8, wherein the concentration of said oligonucleotide $dG_n$ or oligonucleotide $dC_n$ and/or said oligonucleotide $dT_n$ is between 2.5 µM and about 750 µM.

12. The composition of claim 3, wherein:
   a) the poloxamer is present in an amount (v/v %) ranging from about 0.1% to about 3%;
   b) glutamate or a salt thereof is present in a concentration of about 15 mM to about 150 mM; and/or
   c) PVSA is present in an amount (v/v %) of about 0.0001% to about 0.001%.

13. The composition of claim 1, wherein the composition comprises oligonucleotide $dG_n$, and n is an integer selected from 5, 6, 7, 8, 9, 10, 11 or 12, $dT_n$, where n is an integer selected from 5, 6, 7, 8, 9, 10, 11 or 12, potassium glutamate, poloxamer 188, polyvinyl sulfonic acid (PVSA), and a random oligonucleotide hexamer $X_1$-$X_2$-$X_3$-$X_4$-$X_5$-$X_6$.

14. The composition of claim 13, said composition further comprising a reverse transcriptase.

15. A method of amplifying a nucleic acid molecule comprising the addition of an RNA template to a reaction mixture comprising the composition of claim 1 and a reverse transcriptase, incubating the reaction mixture and RNA template, and synthesizing complementary DNA to a portion of or the entire template RNA.

16. A method of reducing the inhibition of reverse transcriptase by heparin comprising the addition of an RNA template to a reaction mixture comprising the composition of claim 1 and a reverse transcriptase, incubating the reaction mixture and RNA template, and synthesizing complementary DNA to a portion of or the entire template RNA, said reaction mixture comprising heparin and at least histidine and/or salts thereof and/or glutamate and/or salts thereof as an additive.

17. A method of reducing the inhibition of reverse transcriptase by tannic acid, wherein the method comprises the addition of an RNA template to a reaction mixture comprising the composition of claim 1 and a reverse transcriptase, incubating the reaction mixture and RNA template, and synthesizing complementary DNA to a portion of or the entire template RNA, said reaction mixture comprising tannic acid and at least poloxamer 188 as an additive.

18. A method of improving the efficiency and sensitivity of reverse transcriptase, wherein the method comprises the addition of an RNA template to a reaction mixture comprising the composition of claim 1 and a reverse transcriptase and incubating the reaction mixture and RNA template to synthesize complementary DNA to all or a portion of the template RNA, said reaction mixture comprising PVSA as an additive.

19. A method of reducing the inhibition of reverse transcriptase by formalin, wherein the method comprises the addition of an RNA template to a reaction mixture comprising the composition of claim 1 and a reverse transcriptase, incubating the reaction mixture and RNA template, and synthesizing complementary DNA to a portion of or the entire template RNA, said reaction mixture comprising formalin and at least histidine and/or a salt thereof as an additive.

20. The composition of claim 1, wherein the nucleotides of said oligonucleotides are at least 60% G and/or C.

21. The composition of claim 1, wherein the nucleotides of said oligonucleotides are at least 60% A and/or T.

22. The composition of claim 1, wherein the composition comprises oligonucleotide $dC_n$, and n is an integer selected from 5, 6, 7, 8, 9, 10, 11 or 12, $dT_n$, where n is an integer selected from 5, 6, 7, 8, 9, 10, 11 or 12, potassium glutamate, poloxamer 188, polyvinyl sulfonic acid (PVSA), and a random oligonucleotide hexamer $X_1$-$X_2$-$X_3$-$X_4$-$X_5$-$X_6$.

* * * * *